United States Patent [19]

Holmgren et al.

[11] Patent Number: 4,583,392

[45] Date of Patent: Apr. 22, 1986

[54] METHOD OF TESTING CONSTRUCTION UNITS WITHIN THE FURNITURE FIELD WITH ASSOCIATED ENVIRONMENTS IN THEIR NORMALLY USED ASSEMBLED STATE AND AN APPARATUS TO BE USED BY THE METHOD

[75] Inventors: Holger Holmgren; Bo Wadling, both of Älmhult, Sweden

[73] Assignee: Inter-Ikea AG, Lucerne, Switzerland

[21] Appl. No.: 606,242

[22] Filed: May 2, 1984

[30] Foreign Application Priority Data

May 10, 1983 [DK] Denmark ............................. 2074/83

[51] Int. Cl.⁴ .............................................. G01N 3/56
[52] U.S. Cl. .............................................. 73/7; 73/12
[58] Field of Search ......................................... 73/7, 12

[56] References Cited

U.S. PATENT DOCUMENTS 2,590,839 4/1952 Clapham ................................... 73/7
2,797,574 7/1957 Rusca et al. ............................... 73/7

FOREIGN PATENT DOCUMENTS 151086 2/1961 U.S.S.R. ..................................... 73/7

Primary Examiner—Anthony V. Ciarlante

[57] ABSTRACT

A method of and apparatus for reproducibly testing the resistance to wear and change in appearance as well as the soil resistance of construction units (4) in full size within the furniture field with associated environments, the construction unit (4) or parts thereof in its full construction being positioned secured on the inner side of a rotatable large drum (1) and subjected to stresses from various stress members (5) located in the drum (1). These stress members are activated by the rotation of the drum. The stress members (5) may for instance be leather balls (5) filled with water or sand and optionally provided with a facing of wearing members (15) of textile materials or another wearing material such as for instance emery cloth, whereafter the number of rotations of the drum are registered and compared with changes arising through natural use.

16 Claims, 6 Drawing Figures

METHOD OF TESTING CONSTRUCTION UNITS WITHIN THE FURNITURE FIELD WITH ASSOCIATED ENVIRONMENTS IN THEIR NORMALLY USED ASSEMBLED STATE AND AN APPARATUS TO BE USED BY THE METHOD

The invention relates to a method of reproducibly testing the resistance to wear and changes in appearance as well as the soil resistance of construction units within the furniture field with associated environments such as the domestic environment, offices, canteens, assembly halls, means for transport etc. in their normally used assembled state and in full size or optionally as scale models such as for instance for an article of furniture with an outer coating of textile and with one or more underlying layers over a frame. The invention also relates to an apparatus for carrying out the method.

The increasing use of new materials during recent years and the quick change to new constructions and combinations of materials within the furniture field with associated environments have caused an increasing demand for new testing methods and testing apparatuses rendering it possible to a higher extent than previously to carry out a test replacing with a good approximation a practice test of the assembled construction units.

A number of various methods with associated apparatuses are known for testing separate qualities of the individual parts of a construction unit. A common problem for a number of these known methods and apparatuses is, however, that the test conditions deviate essentially in several respects from the actual conditions that the parts in question are subjected to in practice. This problem applies for instance to a number of useful qualities of the construction units mentioned above.

Thus methods with associated apparatuses are used for instance for testing the resistance of textiles and other relatively soft, flexible fabrics to wear and change in appearance, where small samples of fabric in planar state are subjected to rubbing against a friction surface irrespective of the shapes in which the fabrics are used in practice and furthermore irrespective of the material layers that the fabrics are to be used together with.

For testing the resistance to wear and change in appearance of carpets and soft floor coverings methods and apparatuses are furthermore known, whereby small drums are coated with the text material on the inside of the peripheral surface. Subsequently, the testing material is subjected to a freely falling four-footed wearing member in the drum during the rotation of said drum. The apparatuses used are, however, of a rather modest size with relatively small samples and wearing members. In addition the samples are mounted in a concavely bent position unnatural compared to the use in practice of said samples which implies that they are subjected to unnatural stresses. Moreover these apparatuses are not suited for testing other types of materials.

The object of the invention is to provide a method and an apparatus for testing especially the wear resistance and change in appearance as well as the soil resistance of construction units within the furniture field with associated environments under conditions as far as possible corresponding to the use conditions in practice of said construction units, including especially their shape and combination with various materials.

The method according to the invention is characterised by positioning the construction unit or parts thereof in its full construction secured on the inner peripheral surface of a rotatable, optionally reversible, large drum, and subsequently by subjecting said unit to the stress of stress members located within the drum and activated by the rotation of the drum in such a manner that they slide on, abut, and/or are dragged across the construction unit, whereby the number of stresses or rotations of the drum necessary for producing a predetermined change in appearance of the construction unit by given test conditions are registered. In this manner the construction unit is tested in its normally used assembled state, whereby an expression close to the practice is obtained of the qualities of the assembled construction unit. Thus it is possible to test the stress of variations both in the outer material and in the underlying materials.

In order to make the test results correspond as much as possible to the actual useful qualities, the test conditions are chosen such that results are obtained which correlate well with the changes in appearance arising in practice for the same construction unit, such as several simultaneously working stress members such as for instance substantially ball-shaped leather balls filled with air, water or sand and provided with a facing of wearing tapes having varying wearing qualities in response to the field of application for the tested construction unit, e.g. textile wearing materials for furniture surfaces for sitting or lying purposes and for instance emery cloth and/or sole materials for floor coverings.

An apparatus according to the invention for reproducibly testing the resistance to wear and changes in appearance as well as the soil resistance of construction units within the furniture field with associated environments such as the domestic environment, offices, canteens, assembly halls, means of transport etc. in their normally used assembled state and in full size or optionally as scale models such as for instance for an article of furniture with an outer coating of textile and with one or more underlying layers over a frame, is according to the invention characterised in that it comprises a rotatable and optionally reversible, large drum supported by supporting means and comprising means for accurately adjusting the number of rotations of the drum and furthermore comprising a number of securing devices situated along the inner circumference of the drum for securing one or more construction units on each device as well as a number of stress members located within the drum. Such an apparatus renders it possible to a great extent to imitate the stresses arising in practice on the construction units in question. Furthermore the apparatus is very flexible with respect to possible test conditions, and it can be used for testing several identical or differing units at the same time. In addition, the apparatus is of a sturdy construction and requires only little time for the testing.

In order to ensure room for any size of all usual construction units in the drum or for sufficiently great parts thereof, whereby a testing close to the actual conditions is possible, the drum may according to the invention be of an internal diameter of the magnitude 900-2000 mm, preferably 1000-1600 mm, especially 1200 mm. Thus four seats or cushions with a 90° displacement along the periphery may be tested simultaneously in a drum of 1200 mm.

In order always to maintain a constant distance between the testing members and consequently to maintain constant falling lengths or a constant movability of the stress members, the securing devices may according to the invention be radially adjustable. Furthermore, in order to make it easy to mount, inspect, and dismount the testing members, the securing devices may according to the invention be axially removable.

According to the invention the securing devices may thus be plates mounted so as to be radially adjustable on axially directed slide bars retainable and axially displaceable in fixed guides on the inner peripheral surface of the drum, said plates comprising fittings or the like means for the securing of the construction units. This embodiment turned out to be a useful embodiment of the securing devices, which facilitates the change between various construction units.

A particularly flexible and relatively inexpensive type of stress members is according to the invention obtained by the stress members being wearing members loosely situated in the drum and freely falling at the rotation of said drum, said wearing members for instance being balls, bags or the like members solid or filled with air, water or sand and of a shape, size, weight, and coating defined in greater details such as for instance substantially ball-shaped, water-filled leather balls of a diameter of 200±10 mm, a weight of 2500±50 g, and optionally provided with wearing tapes of another coating material such as jute fabric, emery cloth or the like material. Experience has shown that such stress members provide results close to practice.

In an apparatus where the tested construction unit is part of a floor coating such as a textile floor coating, the stress members may furthermore according to the invention be coated with materials of a type used for soles, and the various stress members may be made of different coating materials, whereby a stress of the floor coating is obtained which is particularly close to practice.

Stress members may according to the invention furthermore be provided which are suspended on a central suspension shaft in such a manner that they can be dragged across the construction units during the rotation of said units with the drum. In this manner a particular type of stresses is obtained which is particularly suited for constructions units in practice subjected to similar dragging stresses, e.g. door mats.

A simple way of applying especially dragging or particular stresses may according to the invention be obtained by means of an axial rod projecting into the interior of the drum and comprising pendent wearing members such as strips of wearing material or brushes, balls or hose-shaped wearing members being dragged across the construction units during the rotation of said units with the drum. In this manner many different types of stresses can be carried out on the construction units.

Regarding the soil resistance of construction parts the stress members may be substantially cubic members of foam plastics and contain a standardized soiling preparation.

As the supporting means according to the invention are support rollers mounted on a frame so as to run freely, the drum resting and rolling on said support rollers, a sturdy and simple support of the drum is obtained.

The drum may according to the invention be driven by a driving motor pulling directly on a wheel on the central shaft projection of the drum through an endless band or a chain, which forms a simple and efficient power transfer and which furthermore allows an easy adjustment of the number of rotations of the drum.

According to the invention the adjusting means for the rotation of the drum comprise a programmed control unit allowing intermittent running, optionally at varying rates of rotation. As a result it is possible to program in advance the rates of rotation and running periods of a complete test program. As the adjusting means for the rotation of the drum are infinitely variable, an optional adjustment of the number of rotation is obtained.

The drum used may according to the invention be substantially closed both at its peripheral surface and at its end surfaces, and it may comprise openings in its end surfaces allowing a connecting of the interior of the drum to an air conditioning installation. As a result it is possible to maintain a controlled climate within the drum during the testing.

The invention will be described below with reference to the accompanying drawing, in which FIG. 1 is a front perspective view of an apparatus according to the invention, where a construction unit is mounted thereon and stress members are inserted, FIG. 2 corresponds to FIG. 1, but where the securing device is removed, FIG. 3 corresponds to FIG. 1, but including a central suspension shaft with stress members suspended thereon, FIG. 4 illustrates an axial bar with stress members suspended thereon, FIGS. 5a, b, c, d: Examples of stress members, and FIG. 6 is a diagrammatic, rear view of the drum with driving motor, power transfer means, and programmed control unit.

FIG. 1 illustrates an apparatus according to the invention. The apparatus comprises a cylindrical drum 1, which can be made rotating about its own axis and which rests on four supporting means 2. These supporting means are shaped as freely running rollers individually mounted in brackets 12 supported by a rigid frame 11. The drum comprises a self-supporting relatively rigid mantle 13 strengtened on the outside by means of two hoops 14. These hoops 14 serve simultaneously as rails for the support rollers 2. The above drum furthermore comprises two end walls, viz. a rear end wall 26 and a front end wall 27, respectively. The drum is of an internal diameter of approx. 1200 mm and an axial length of approx. 650 mm. Four devices 3 are located along the inner peripheral surface 9 of the drum with 90° displacement for the securing of the construction units 4 to be tested. Each securing device 3 comprises a plate 6 mounted parallel to an axial plane for the drum 1 on glide bars 7. The construction unit 4 to be tested is mounted on the plate 6 with the testing surface facing the interior of the drum by means of fittings 10. The plate 6 is radially displaceable in such a manner that the surface of the construction unit 4 to be tested is substantially positioned at a predetermined distance from the axis of symmetry of the drum. The glide bars 7 mounted on the plate 6 are retained and axially displaceable in fixed guides 8 on the inner peripheral surface 9 of the drum in such a manner that the entire plate 6 with the construction unit 4 can be drawn outwards into a position outside the drum 1 by means of a handle 24, cf. FIG. 2, whereby the mounting, the dismounting, and the inspection of the construction unit 4 are essentially facilitated. The apparatus furthermore comprises a number of stress members 5 of varying shapes, some shapes appearing from the FIGS. 5a, b, c, and d. FIG. 1 illustrates three such stress members 5 loosely situated in the drum 1 in a position typical for an idle drum. The stress members 5 shown are leather balls filled with water and provided with wearing tapes 15 in the form of jute fabric. The balls 5 are only partially filled with water and of a diameter of approx. 200 mm and a weight of approx. 2500 g. During the rotation of the drum at a suitable rate of rotation these balls can follow said rotation so far up the peripheral surface of the drum that they fall down on the construction units 4 almost from the top of the interior of the drum. FIG. 3 illustrates another type of stress members, viz. elongated wearing members in the form of bands 18 or long hoses 29 filled with sand, cf. the FIGS. 4 or 5c, and suspended on a central suspension shaft 16. The stress members 18, 29 are suspended in rings 30 rotatable about the suspension shaft 16 in such a manner that they cannot be wound about the shaft when said shaft rotates with the drum. In this embodiment, the stress members are dragged across the construction units.

As illustrated in FIG. 4 the stress members 18, 29 can also be suspended on an axial rod 17 inserted through an opening 28 in the front end wall 27.

FIG. 5 illustrates examples of differently shaped stress members. Thus FIG. 5a illustrates the above ball-shaped stress members, which may be filled with either air, water or sand and be of different diameters, and the outer material of which for instance may be leather, plastics, rubber or textile optionally provided with bands of textile material, emery cloth or another material.

FIG. 5b illustrates a bag-shaped stress member for instance filled with water or sand. This stress member is provided with a contraction in the middle portion in such a manner that two coherent lumps are formed. The size and the outer material of the bag may be varied, and the bag can be more or less filled.

Figure 6:
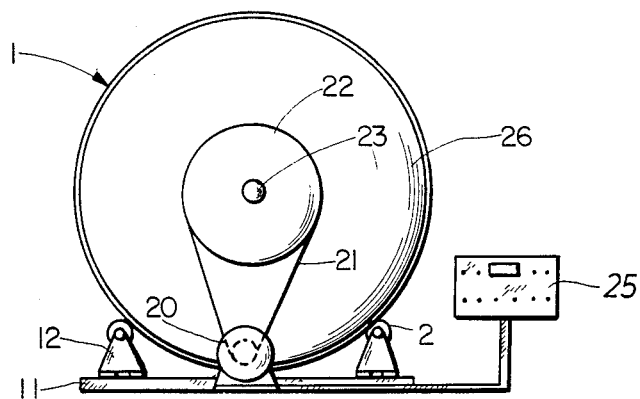
Figure 3:
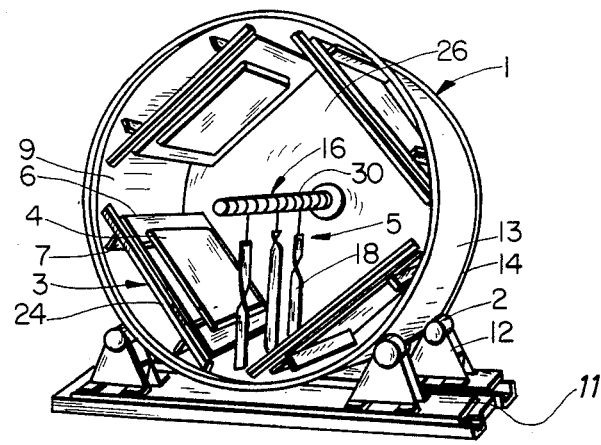
Figure 4:
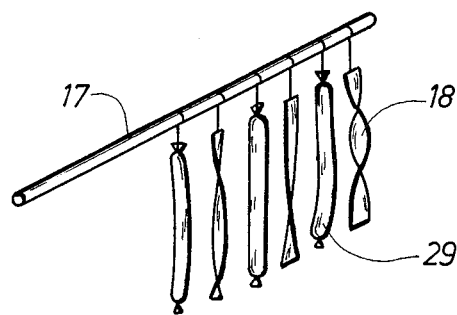
Figure 5A:
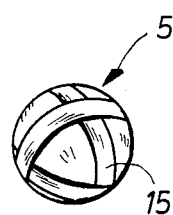
FIG. 5d illustrates a hose-shaped member, which can vary in size, material, and filling too.
FIG. 5c illustrates a substantially cubic member of foam plastics such as for instance polyurethane foam plastics suited for receiving and releasing great amounts of soil such as for instance standardized soil according to British standard. Such stress members allow a testing of the soil tendency of the construction units.
Figure 5B:
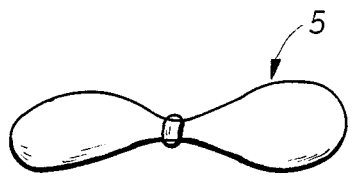
Figure 5C:
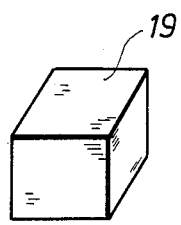
Figure 5D:

The drum is made rotating by means of a driving motor 20, cf. FIG. 6. This driving motor transfers its torque to a wheel 22 through power transferring means such as for instance an endless band 21. The wheel 22 is fixedly connected to the rear end wall 26 of the drum. The number of rotations of the drum is adjustable and controllable by means of a programmed control unit 25 adjustable to intermittent running of the drum at varying rates of rotation.

Figure 1:
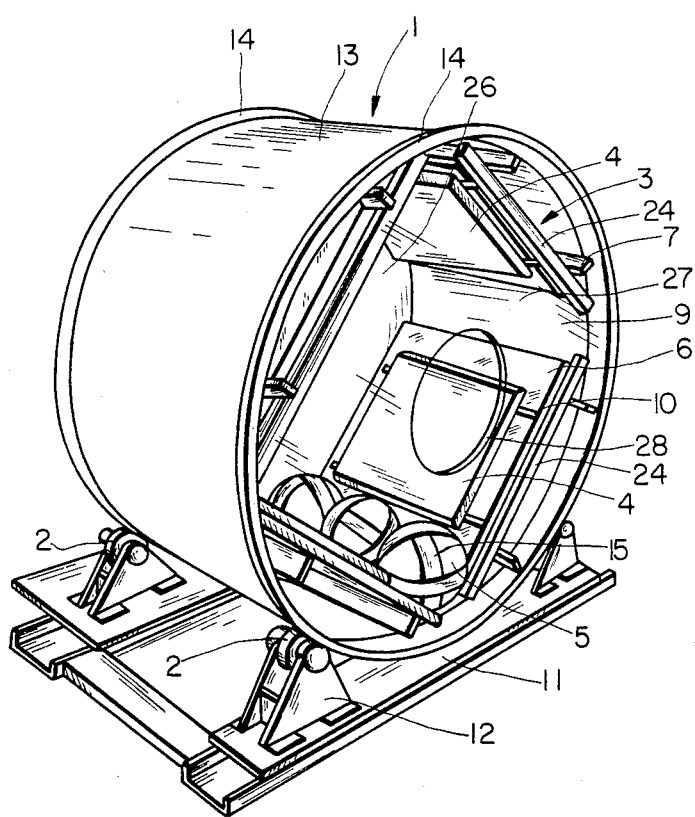
Figure 2:
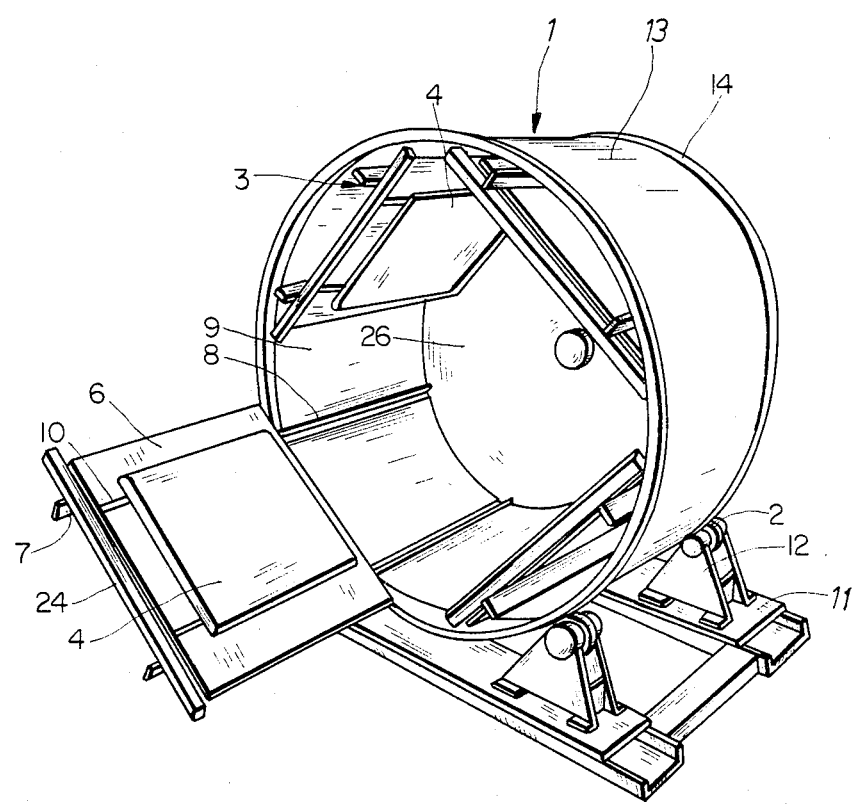

In FIG. 1, the front end wall 27 of the drum is made of transparent plastics and comprises a central opening 28. This opening may be used for communication with a conditioning installation (not shown) controlling the temperature and/or the humidity within the drum, or it may be used for insertion of the stress members on an axial rod 17. The end wall is besides openable or detachable for an insertion and removal of the construction units 4.

When running a test, the construction units 4 are secured in the drum 1. Then the drum is provided with the selection of stress members 5 suitable for the test in question according to experience. Subsequently, the drum is made rotating at a suitable rate of rotation either stepwise a predetermined number of rotations at a time, where the construction units are inspected after each step, or a number of rotations of the drum determined in advance. Now the construction units are removed for a final inspection and for instance compared with standard samples. The tests run up till now have shown a good agreement with the wear patterns and changes in appearance known from use of the construction units in practice. Experience thus taught that a number of rotations for the drum of approx. 17 r/m and with three stress members of the leather ball type of a diameter of 200 mm and filled with water to a weight of 2500 g and with three wearing tapes mounted thereon of woven jute in 5 cm width on each ball usually allow a determination of the resistance to wear and change in appearance of an upholstered furniture unit after approx. 20,000 to 30,000 rotations in the drum.

We claim:

1. A method of reproducibly testing the resistance to wear and changes in appearance as well as the soil resistance of construction units within the furniture field with associated environments such as the domestic environment, offices, canteens, assembly halls, means of transport and the like in their normally used assembled state and in full size or optionally as scale models such as for an article of furniture with an outer coating of textile and with one or more underlying layers over a frame, said method comprising positioning a construction unit (4) or parts thereof in its full construction on an inner peripheral surface (9) of a rotatable, optionally reversible, large drum (1), adjustably securing said construction unit or parts thereof radially to position same a predetermined distance from the axis of symmetry of the drum, and subsequently subjecting said unit or parts thereof to the stress of stress members (5) located within the drum and activated by the rotation of the drum in such a manner that they slide on, abut, and/or are dragged acrosss the construction unit or parts thereof (4), whereby the number of stresses or rotations of the drum necessary for producing a predetermined change in appearance of the construction unit or parts thereof by given test conditions are registered.

2. A method as claimed in claim 1 for testing the furniture surfaces for sitting and lying purposes, by employing several simultaneously working stress members (5) such as substantially ball-shaped leather balls (5) filled with air, water or sand and provided with a facing of wearing tapes of textile materials, said various stress members optionally being made of various facing materials.

3. A method as claimed in claim 1 for testing floor constructions such as textile floor coverings, by using several simultaneously working stress members (5) such as substantially ball-shaped leather balls (5) filled with air, water or sand and provided with a facing of wearing tapes (15) of emery cloth and/or sole materials, said various stress members (5) having different facing materials.

4. An apparatus for reproducibly testing the resistance to wear and changes in appearance as well as the soil resistance of construction units within the furniture field with associated environments such as the domestic environment, offices, canteens, assembly halls, means of transport and the like in their normally used assembled state and in full size or optionally as scale models such as for an article of furniture with an outer coating of textile and with one or more underlying layers over a frame, said apparatus comprising a rotatable and optionally reversible large drum (1) supporting means (2) for supporting the drum, means for accurately adjusting the number of rotations of the drum, a number of securing devices (3) situated along the inner circumference of the drum for securing one or more construction units (4) on each device, said securing devices being radially adjustable and axially removable, and a number of stress members (5) located within the drum.

5. An apparatus as claimed in claim 4, wherein the drum (1) is of an internal diameter of the magnitude 900–2000 mm, preferably 1000–1600 mm, especially 1200 mm.

6. An apparatus as claimed in claim 4, wherein the securing devices (3) are plates (6) mounted so as to be radially adjustable on axially directed slide bars (7) retainable and axially displaceable in fixed guides (8) on the inner peripheral surface (9) of the drum, said plates comprising fittings (10) or the like means for the securing of the construction units (4).

7. An apparatus as claimed in claim 4, wherein the stress members (5) are wearing members loosely situated in the drum and freely falling at the rotation of said drum, said wearing members for instance being balls, bags or the like members solid or filled with air, water or sand and of a shape, size, weight, and coating defined in greater details such as for instance substantially ball-shaped, water-filled leather balls (5) of a diameter of 200±10 mm, a weight of 2500±50 g, and optionally provided with wearing tapes (15) of another coating material such as jute fabric, emery cloth or the like material.

8. An apparatus as claimed in claim 4, and where the tested construction unit (4) is part of a flooring such as a textile floor covering, wherein the stress members (5) are coated with sole material, and that the various stress members are optionally made of different coating materials.

9. An apparatus as claimed in claim 4, wherein it comprises stress members (5) suspended on a central suspension shaft (16) in such a manner that they can be dragged across the construction units (4) during the rotation of said units (4) with the drum (1).

10. An apparatus as claimed in claim 4, wherein there is an axial rod (17) projecting into the interior of the drum and comprising pendent wearing members (18) such as strips of wearing material or brushes, balls or hose-shaped wearing members being dragged across the construction units (4) during the rotation of said units (4) with the drum.

11. An apparatus as claimed in claim 4, especially for testing the soil resistance of the construction units (4), wherein the stress members (5) are substantially cubic members (19) of foam plastics and containing a standardized soiling preparation.

12. An apparatus as claimed in claim 4, wherein the supporting means (2) are support rollers mounted on a frame (11) so as to run freely, the drum (1) resting and rolling on said support rollers.

13. An apparatus as claimed in claim 4, wherein the drum is driven by a driving motor (20) pulling directly on a wheel (22) on the central shaft projection (23) of the drum through an endless band (21) or a chain.

14. An apparatus as claimed in claim 4, wherein the adjusting means for the rotation of the drum comprise a programmed control unit (25) allowing intermittent running, optionally at varying rates of rotation.

15. An apparatus as claimed in claim 14, wherein the adjusting means for the rotation of the drum is infinitely variable.

16. An apparatus as claimed in claim 4, wherein the drum used is substantially closed both at its peripheral surface and at its end surfaces, and that it comprises openings in its end surfaces allowing a connecting of the interior of the drum to an air conditioning installation.

* * * * *